(12) United States Patent
Suzuta

(10) Patent No.: US 6,592,572 B1
(45) Date of Patent: Jul. 15, 2003

(54) SURGICAL OPERATION APPARATUS

(75) Inventor: Toshihiko Suzuta, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 327 days.

(21) Appl. No.: 09/716,691

(22) Filed: Nov. 20, 2000

(30) Foreign Application Priority Data

Nov. 22, 1999 (JP) ............................................ 11-331623
Nov. 22, 1999 (JP) ............................................ 11-331624

(51) Int. Cl.$^7$ .............................................. A61B 17/00
(52) U.S. Cl. ............................ 606/1; 606/208; 294/115
(58) Field of Search ............................ 606/1, 170, 174, 606/205, 207; 600/104; 74/490.01, 490.02, 490.05, 490.06; 81/387, 393; 294/106, 115; 901/31, 32, 38

(56) References Cited

U.S. PATENT DOCUMENTS

| | | | |
|---|---|---|---|
| 2,028,635 A | | 1/1936 | Wappler |
| 2,535,215 A | * | 12/1950 | Klenk ........................ 81/347 |
| 5,282,826 A | | 2/1994 | Quadri et al. |
| 5,350,391 A | | 9/1994 | Iacovelli et al. |
| 5,383,888 A | * | 1/1995 | Zvenyatsky et al. ........ 606/206 |
| 5,540,706 A | | 7/1996 | Aust et al. |
| 5,618,294 A | | 4/1997 | Aust et al. |
| 5,792,135 A | * | 8/1998 | Madhani et al. ................ 606/1 |
| 6,063,103 A | * | 5/2000 | Hashiguchi .................. 606/205 |
| 6,331,181 B1 | * | 12/2001 | Tierney et al. ............... 606/130 |
| 6,470,236 B2 | * | 10/2002 | Ohtsuki ....................... 700/247 |

FOREIGN PATENT DOCUMENTS

| | | |
|---|---|---|
| DE | 197 03 600 A1 | 8/1998 |
| EP | 0 306 123 A1 | 3/1989 |
| EP | 0 640 319 A1 | 3/1995 |
| FR | 2 681 775 A1 | 4/1993 |

* cited by examiner

Primary Examiner—David O. Reip
Assistant Examiner—D. Jacob Davis
(74) Attorney, Agent, or Firm—Scully, Scott, Murphy & Presser

(57) ABSTRACT

A surgical operation apparatus according to the present invention comprises an insert section, a first jaw that has a first grip section, and that turns about a first pivot provided at the insert section, a second jaw that has a second grip section, and that turns about a second pivot provided at the first jaw, the second grip section forming a contacted/spaced face to be contacted or spaced relevant to a grip object in collaboration with the first grip section, a first driving rod connected to a first jaw, a second driving rod connected to a second jaw, and a driving mechanism, the driving mechanism being adopted to drive the first and second driving rods to be advanced or retracted.

18 Claims, 7 Drawing Sheets

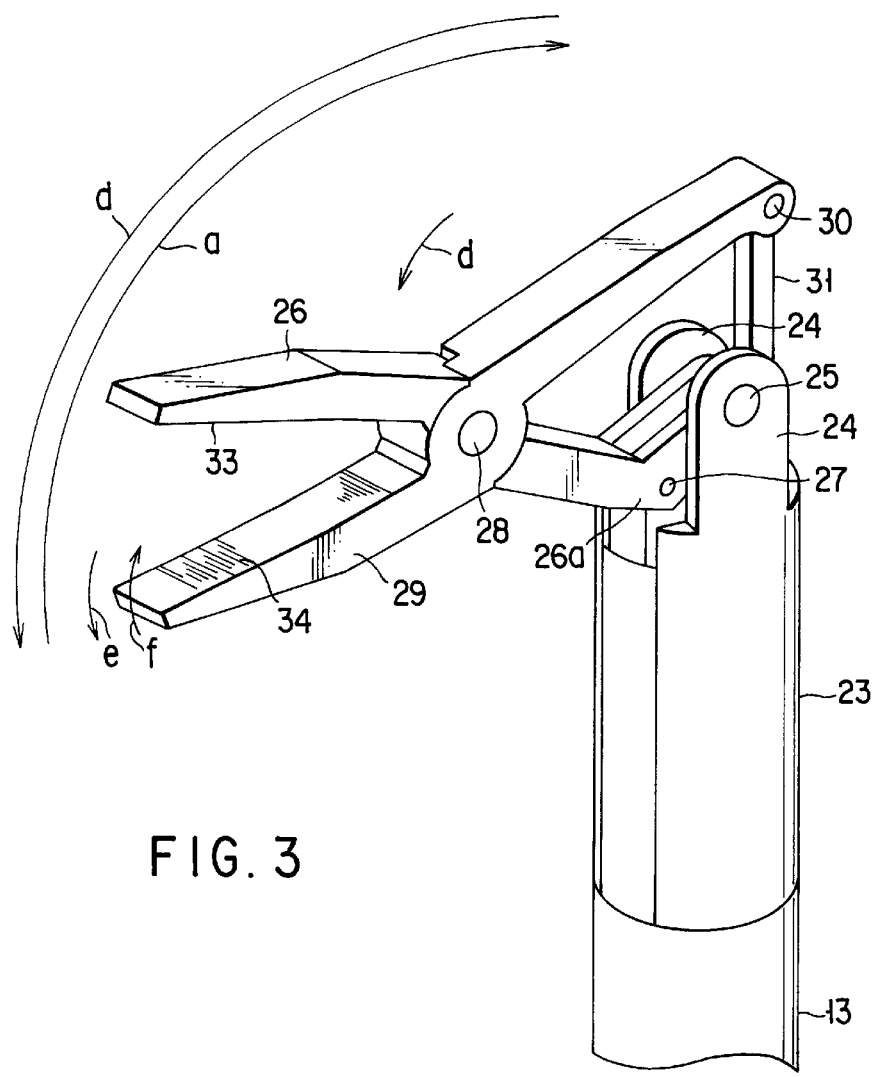
FIG. 3
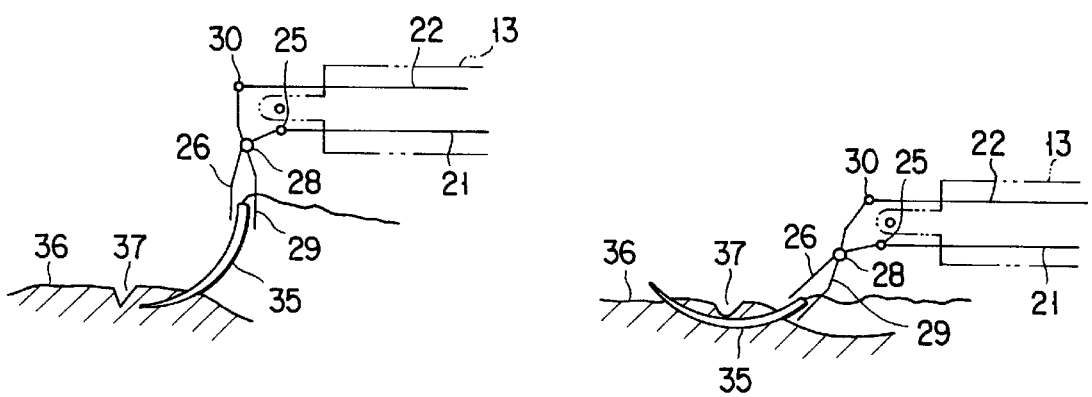
FIG. 4A
FIG. 4B

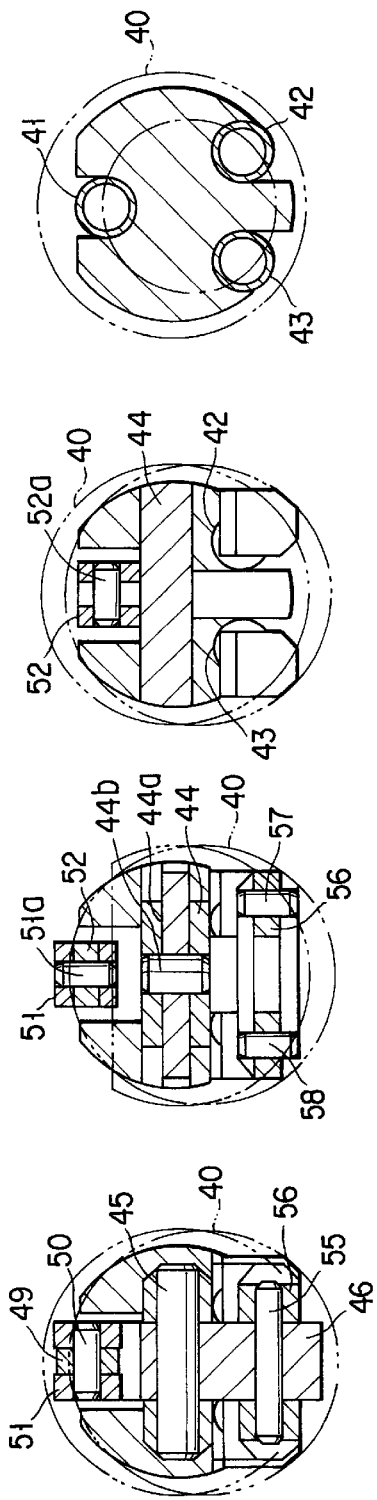
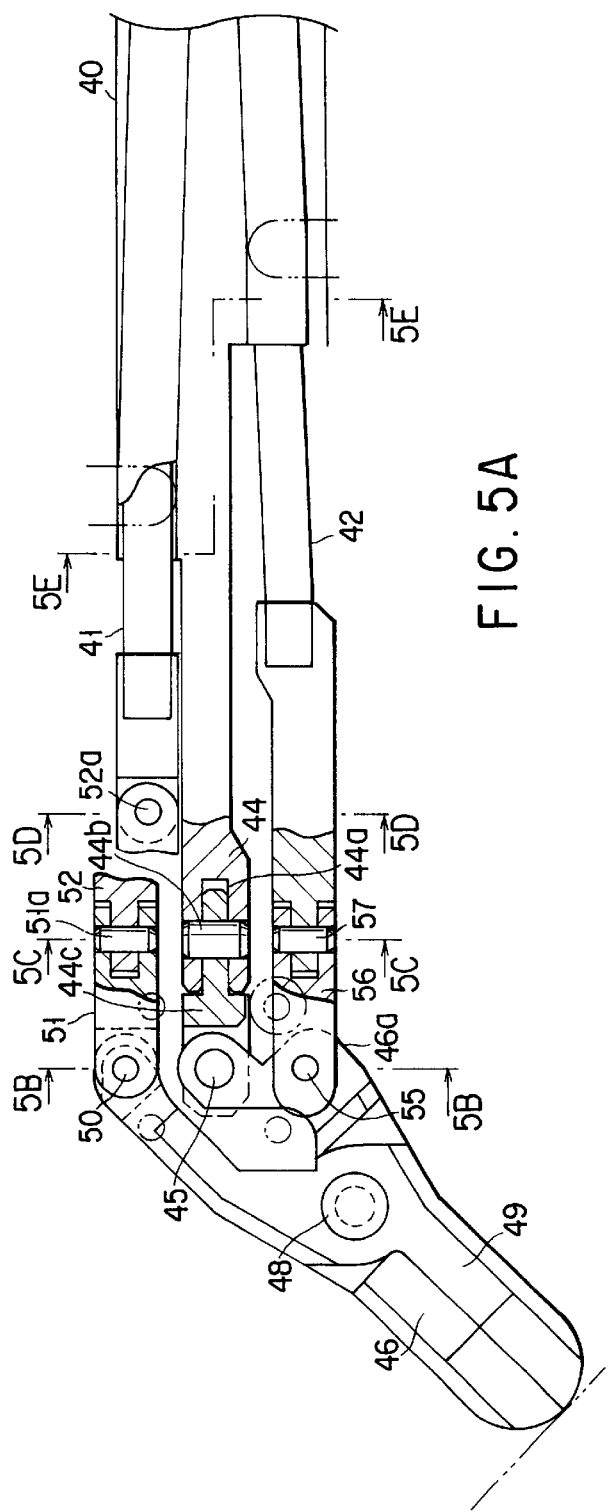

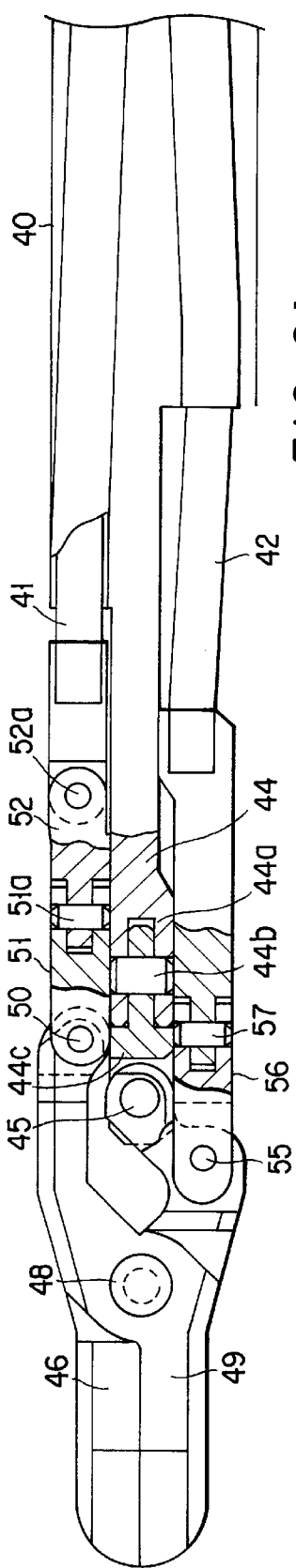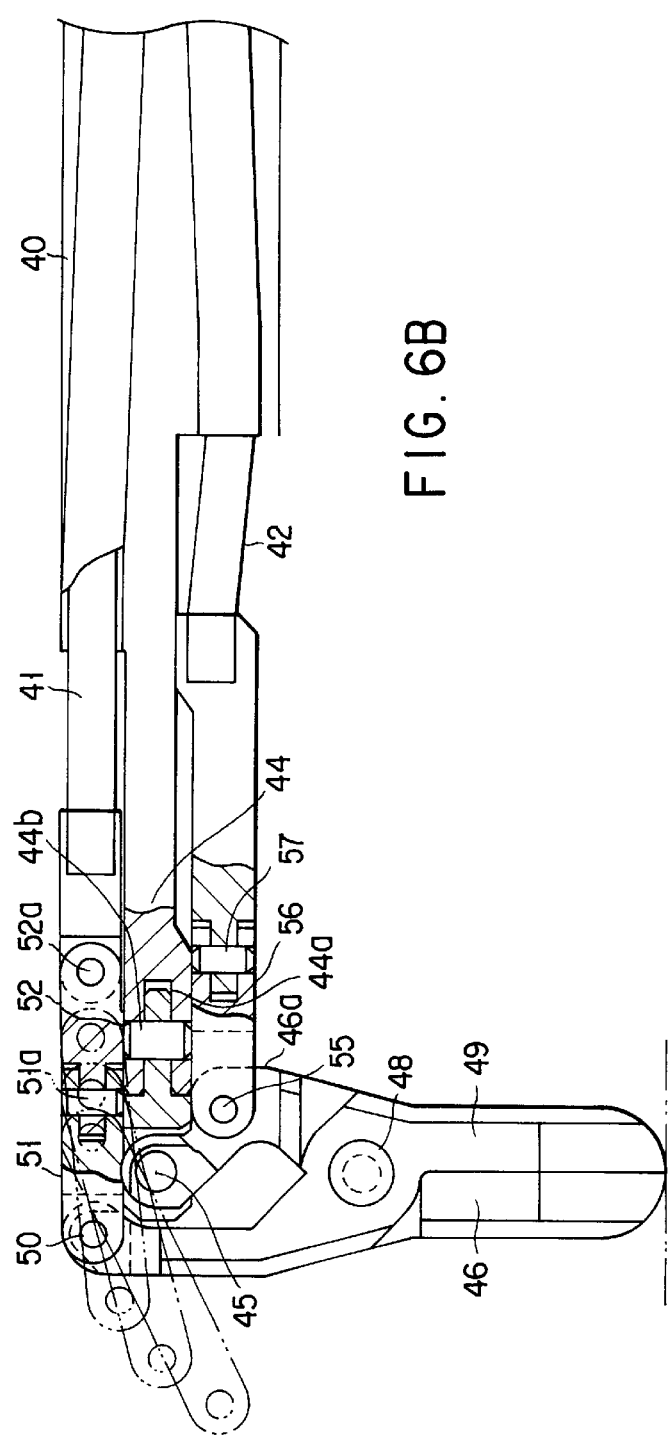

SURGICAL OPERATION APPARATUS

CROSS-REFERENCE TO RELATED APPLICATIONS

This application is based upon and claims the benefit of priority from the prior Japanese Patent Applications No. 11-331623, filed Nov. 22, 1999; and No. 11-331624, filed Nov. 22, 1999, the entire contents of which are incorporated herein by reference.

BACKGROUND OF THE INVENTION

The present invention relates to a surgical operation apparatus for remotely transmitting an operation of a master manipulator that a surgeon operates to a sub-manipulator, thereby performing surgical operation.

In a master/slave system, an operation of a master manipulator that the surgeon operates while observing an endoscopic image of a diseased site is recognized by means of a computer for computing a position of the master manipulator. This recognized signal is transmitted to a slave manipulator via an optical fiber cable and a slave manipulator control computer so as to perform a surgical operation.

This master/slave system is disclosed in the specifications of U.S. Pat. Nos. 5,792,135, 5,797,900, and 5,807,377. These specifications show a slave manipulator, wherein a support member is turnably provided at a tip end of an insert section to be inserted into a cavity via a pivot section, and a grip member for gripping a tissue or a treatment instrument is turnably provided at this support member.

A driving section is provided at a proximal end of the insert section, and a plurality of motors are incorporated in this driving section. These motors are hung on the support member at the tip end of the insert section and a pulley of the grip member via a wire hung on the pulley. In addition, the rotational force of the motor is transmitted via a plurality of wires hung on the pulley so as to turn the support member at the tip end of the insert section and to openably drive the grip member.

However, the aforementioned conventional manipulator transmits the rotational force of the motor incorporated in the driving section via a plurality of wires hung on the pulley so as to drive the support member and grip member at the tip end.

That is, a plurality of wires are inserted into the insert section, and these wires are pushed or pulled by means of the rotational force of the motor. Therefore, there is a problem that a space is required for retractably inserting wires into the insert section, and the diameter of the insert section increases. In addition, since wires are expanded when a tensile stress is applied, even if the motor is driven to rotate, the support member and grip member may not work well. Further, it is difficult to cause the support member and grip member to reliably approach a target site, and to actuate them finely.

BRIEF SUMMARY OF THE INVENTION

It is an object of the present invention to provide a surgical operation apparatus capable of improving approach properties for a treatment site in a cavity, and improving the degree of freedom for treatment.

The above object of the present invention is achieved by the following surgical operation apparatus. That is, a surgical operation apparatus according to the present invention comprises: an insert section to be inserted into a body; a first jaw having a first grip section, the first jaw being turned about a first bearing provided at a tip end of the insert section; a second jaw having a second grip section, the second jaw being turned about a second bearing provided at the first jaw, the second grip section forming a contacted/spaced face to be contacted or spaced relevant to a grip object in collaboration with the first grip section; a first driving rod connected to the first jaw, the first driving rod advancing or retracting the jaw along the insert section, thereby turning the first jaw; a second driving rod connected to the second jaw, the second driving rod advancing or retracting along the insert section, thereby turning the second jaw by; driving means provided at a proximal end of the insert section, the driving means being adopted to drive the first and second driving rods to be advanced or retracted.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a perspective view showing essential portions of the slave manipulator shown in FIG. 2;

FIG. 4A and FIG. 4B are views showing a state in which the slave manipulator shown in FIG. 2 is used;

FIG. 5A is a vertical side view having a partial cross section of a tip end of the slave manipulator according to the second embodiment of the present invention;

FIG. 5B is a cross section taken along the line 5B—5B shown in FIG. 5A;

FIG. 5C is a cross section taken along the line 5C—5C shown in FIG. 5A;

FIG. 5D is a cross section taken along the line 5D—5D shown in FIG. 5A;

FIG. 5E is a cross section taken along the line 5E—5E shown in FIG. 5A;

FIG. 6A is a side view having a partial cross section showing a state in which a treatment section of the slave manipulator shown in FIG. 5A is set straight;

FIG. 6B is a side view having a partial cross section of a state in which the treatment section of the slave manipulator shown in FIG. 5A is turned downward at a right angle;

DETAILED DESCRIPTION OF THE INVENTION

Figure 1:
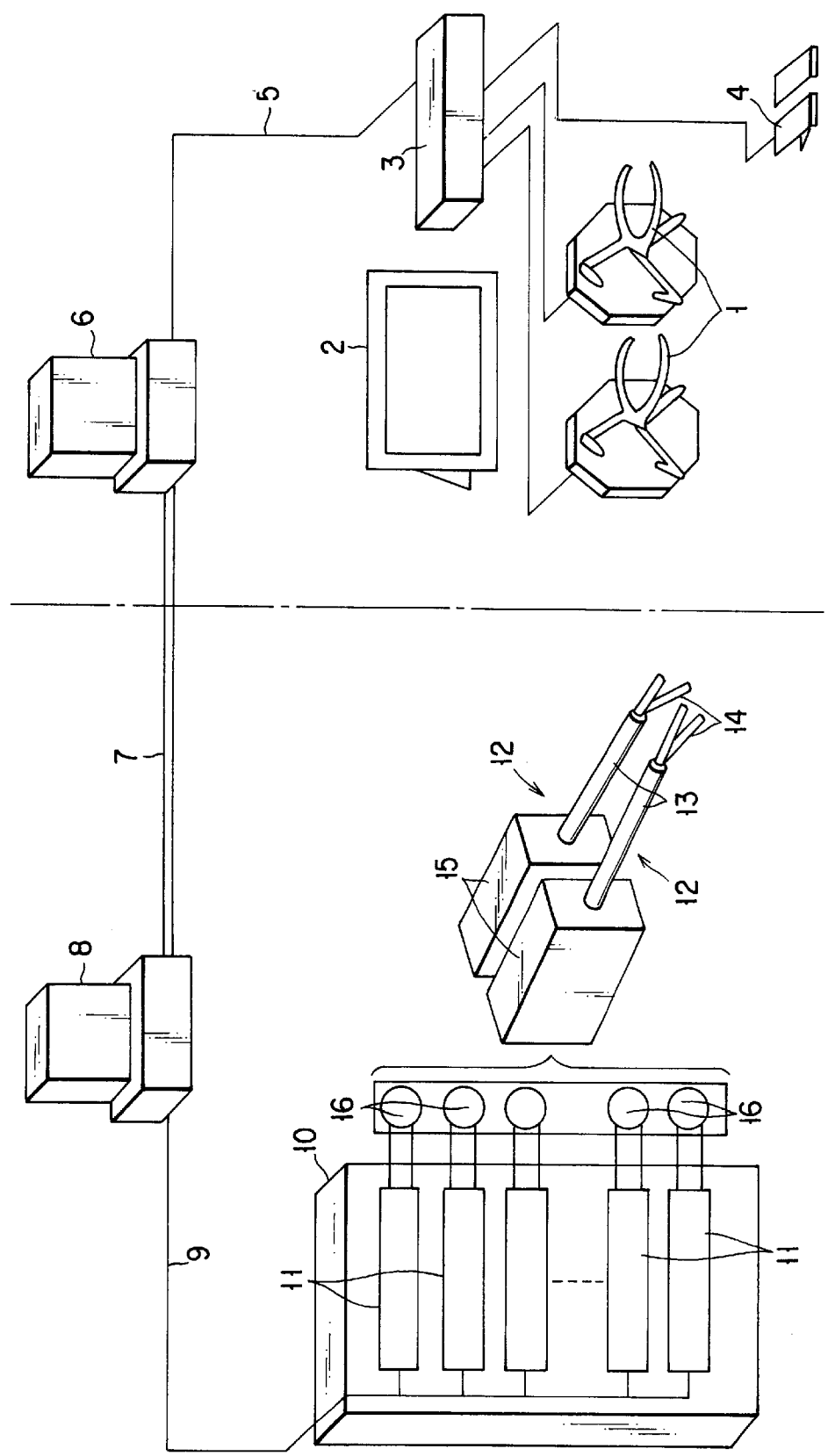
FIG. 1 is a schematic view showing a configuration of a master/slave system.

Hereinafter, one embodiment of the present invention will be described with reference to the accompanying drawings. FIG. 1 to FIG. 4A and FIG. 4B show a first embodiment of the present invention. By referring now to a master/slave system shown in FIG. 1, reference numeral 1 denotes a pair of left and right manipulators, and reference numeral 2 denotes a monitor on which an endoscopic image is acquired. A pair of master manipulators 1 is designed so that a surgeon can operate the manipulators with both hands while observing the monitor 2. When this master manipulator 1 is moved in the XY and Z directions, its position data is inputted to a position detector 3. A master manipulator control foot switch 4 is connected to this position detector 3.

The position detector 3 is connected to a master manipulator position computing computer 6 via a signal cable 5, and the master manipulator position computing computer 6 is connected to a slave manipulator control computer 8 installed remotely from the master manipulator 1 via an optical fiber cable 7. Further, the slave manipulator control computer 8 is connected to a motor unit 10 via a signal cable 9.

14 servo units 11 are provided inside of the motor unit 10 in the present embodiment. Reference numeral 12 denotes a pair of slave manipulators that are a surgical operation apparatus corresponding to the master manipulators 1. The pair of slave manipulators 12 have the same structure as that of master manipulator. Each manipulator consists of: an insert section 13; a treatment section 14 provided at the tip end of this insert section 13; and a slave driving section 15 provided at the proximal end of the insert section 13, the slave driving section 15 for driving the treatment section 14, wherein seven servo motors 16 are provided at each slave driving section 15.

The insert section 13 of the pair of slave manipulators 12 is inserted into a patent's cavity together with an endoscope (not shown), and a surgeon operates the master manipulator 1 with both hands while observing the endoscopic image on the monitor 2, whereby the slave manipulators 12 are actuated according to the operation so that a surgical operation can be performed.

Figure 2:
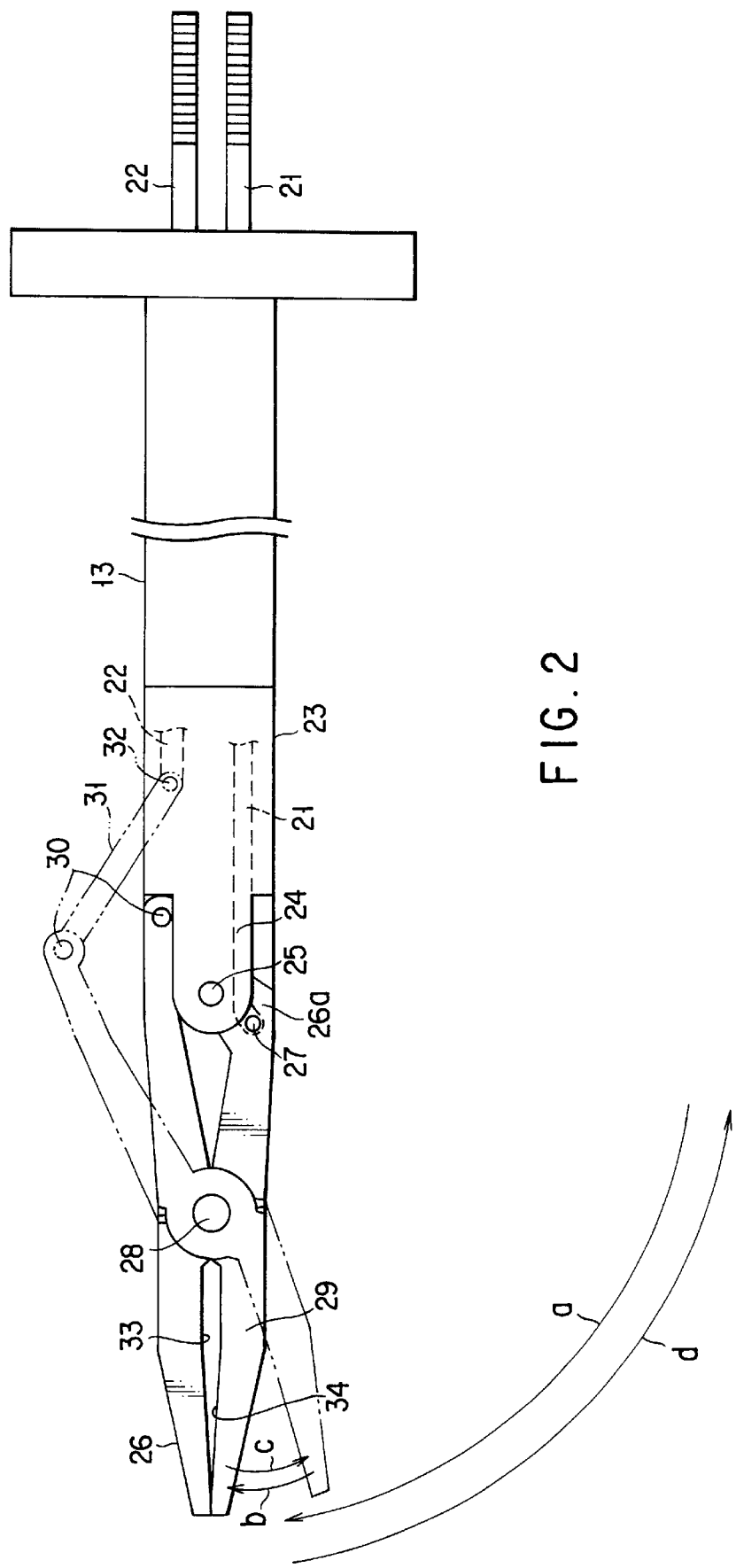
FIG. 2 is a side view showing essential portions of a surgical operation apparatus as a slave manipulator according to a second embodiment of the present invention.
Figure 7:
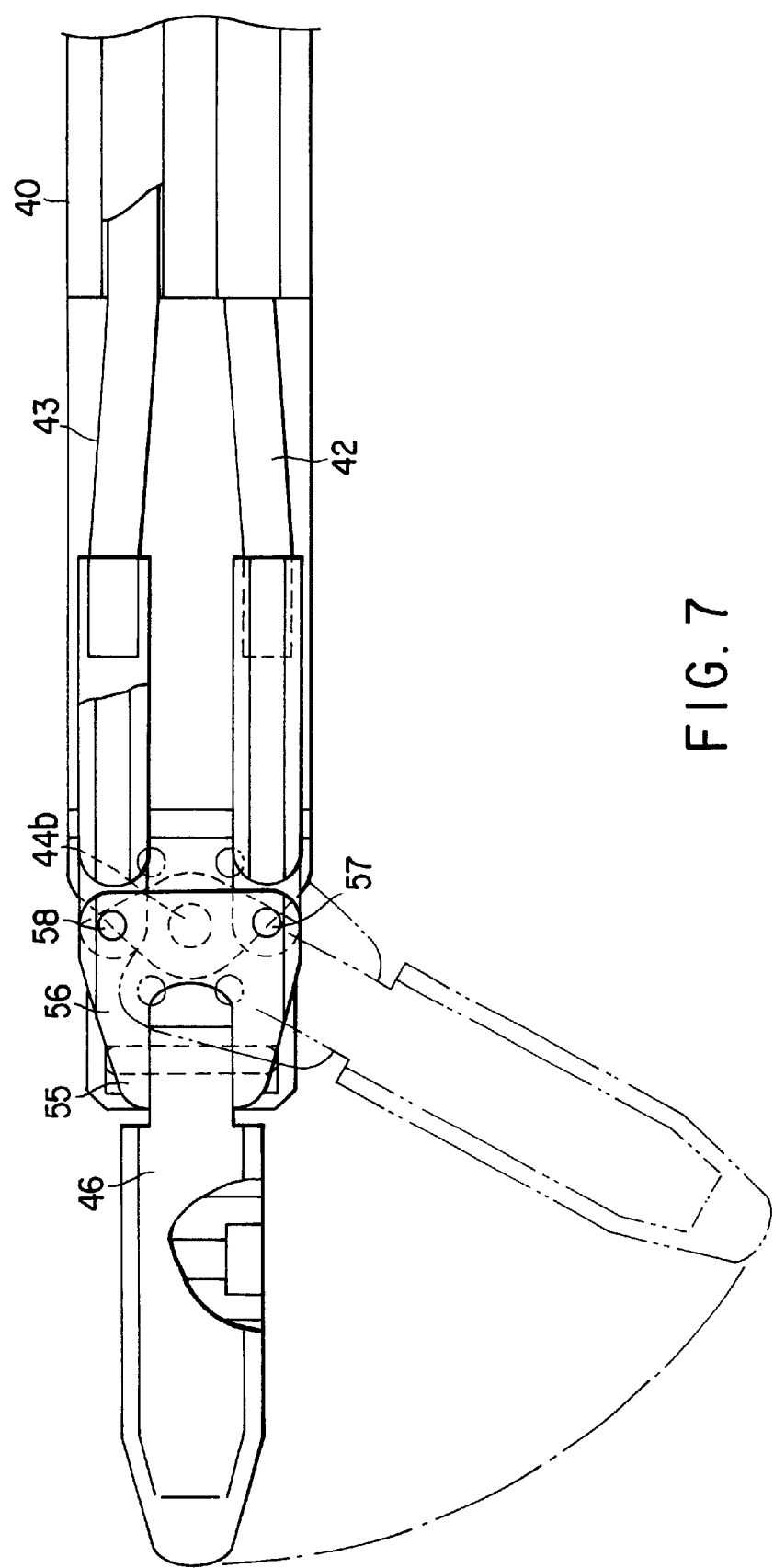
FIG. 7 is a plan view showing a state in which the treatment section of the slave manipulator shown in FIG. 5A is turned in the counterclockwise direction.

Now, slave manipulators 12 will be described with reference to FIG. 2 and FIG. 3. The insert section 13 is composed of an elongated metallic pipe of short diameter. A first driving rod 21 and a second driving rod 22 that are made of metallic rods of short diameter are inserted into this pipe in parallel to each other. These first and second driving rods 21 and 22 are disposed symmetrically at both sides while a axial center of the insert section 13 is sandwiched therebetween, and are retractable independently in an axial direction.

A treatment section support tube 23 is connected to the tip end of the insert section 13. At this treatment section support tube 23, there is integrally provided a pair of support sections 24 having their rigidity, the support sections protruding forward. Both ends of a first pivot pin 25 are fixed between tip ends of the pair of support section 24, and a proximal end of a first jaw 26 is turnably pivoted at the intermediate part of this first pivot pin 25. A bent section 26a is provided at the proximal end of the first jaw 26, and a tip end of the first driving rod 21 is connected to a bend section 26a of the first jaw 26 by means of a first connecting pin 27.

A second jaw 29 is turnably connected at the intermediate part of the first jaw 26 by means of a second pivot pin 28, and the first jaw 26 and the second jaw 29 are turnable with the second pivot pin 28 being a fulcrum. One end of the connecting member 31 is turnably connected at the proximal end of the second jaw 29 via the second connecting pin 30, and the other end of the connecting member 31 is turnably connected at the tip end of the second driving rod 22 via a third connecting pin 32.

At the tip ends of the first and second jaws 26 and 29, contacted/spaced faces configuring first and second grip sections 33 and 34 for gripping a tissue or a treatment instrument are provided in opposite to each other. Fine irregularities or teeth are formed on these contacted/spaced faces.

According to the thus configured slave manipulator 12, when the first driving rod 21 is advanced, the first jaw 26 is pushed forward via the first connecting pin 27. Thus, the first jaw 26 is turned in the direction indicated by the arrow 'a' with the first pivot pin 25 being a fulcrum. Conversely, when the second driving rod 22 is retracted, the proximal end of the second jaw 29 is pulled backward via a connecting member 31. Thus, the second jaw 29 turns in the direction indicated by the arrow 'b' with the second pivot pin 28 being a fulcrum. Therefore, the first and second jaws 26 and 29 protrudes in an extension direction of the insert section 13 as indicated by solid line shown in FIG. 2, and the first and second grip sections 33 and 34 close.

In addition, from this state, when the second driving rod 22 is advanced while the first driving rod 21 remains, the proximal end of the second jaw 29 is pushed forward via the connecting member 31. Thus, the second jaw 29 turns in the direction indicated by the arrow 'c' with the second pivot pin 28 being a fulcrum, and the first and second grip sections 33 and 34 open. Therefore, the first and second driving rods 21 and 22 are advanced and retracted, whereby the first and second jaws 26 and 29 can be opened or closed.

Next, when the first driving rod 21 is retracted, the first driving rod 21 pulls a bent section 26a of the first jaw 26. Thus, the first jaw 26 turns in the direction indicated by the arrow 'd' with the first pivot pin 25 being a fulcrum, and turns at a substantial right angle relevant to an axle of the insert section 13. In addition, when the second driving rod 22 is advanced in this state, the proximal end of the second jaw 29 is pushed via the connecting member 31. Thus, the second jaw 29 turns in the direction indicated by the arrow 'e' shown in FIG. 3 with the pivot pin 28 being a fulcrum, and the first and second grip sections 33 and 34 open.

Further, conversely, when the second driving rod 22 is retracted, the proximal end of the second jaw 29 is pulled via the connecting member 31. Thus, the second jaw 29 turns in the direction indicated by the arrow 'f' shown in FIG. 3 with the second pivot pin 28 being a fulcrum, and the first and second grip sections 33 and 34 close.

Therefore, even if the first and second jaws 26 and 29 are forced to be turnably displaced at a substantial right angle relevant to the axle of the insert section 13, the first and second jaws 26 and 29 are turned, whereby the first and second grip sections 33 and 34 can be opened or closed.

Although the advancement or retraction of the first and second driving rods 21 and 22 is driven by converting a rotational movement of the servo motor 16 incorporated in the slave driving section 15 into a linear movement by means of a wire provided inside of the slave driving section 15 and a pulley having the wire hung thereon (not shown), advancement and retraction driving means of the first and second driving rods 21 and 22 is not limited.

Now, a method of suturing a dissection site of a tissue using a master/slave system will be described here. FIG. 4A shows a state in which a first driving rod 21 is retracted, and first and second jaws 26 and 29 are turned at a substantial right angle relevant to an axle of the insert section 13 and a state in which a threaded suture needle 35 is gripped by the first and second gripped sections 33 and 34. In this state, when the suture needle 35 is positioned in the vicinity of a dissection site 37 of a tissue 36, whereby the tip end of the insert section 13 is pushed up in the direction of the tissue 36, the suture needle 35 is punctured at the tissue 36.

Next, when the first driving rod 21 is advanced, the proximal end of the first jaw 26 is pushed. Thus, the first jaw 26 turns forward with the first pivot pin 26 being a fulcrum. As shown in FIG. 4B, the suture needle 35 is punctured at the tissue 36 having the dissection site 37, and the tip end of the suture needle 35 protrudes from a top layer of the tissue 36. In this way, the first and second jaws 26 and 29 can be turned in the axial direction of the suture needle 35, and the suture needle 35 can be easily punctured.

In addition, as described previously, in a state in which the first and second jaws 26 and 29 are oriented in the axial direction of the insert section 13 or are turnably displaced at a substantial right angle relevant to the axle, the first and second jaws 26 and 29 are turned, whereby the first and second grip sections 33 and 34 can be opened or closed, or can approach a target site reliably. The tissue 36 can be easily not only sutured but also can be easily gripped or released.

FIG. 5A to FIG. 7 each show a second embodiment of the present invention. As illustrated, as in the first embodiment, the slave manipulator according to the present embodiment is also actuated by means of the master manipulator 1. In addition to the fact that the first and second jaws according to the first embodiment are opened or closed and are turned in a vertical direction, the first and second jaws can be turned in a transverse direction.

As shown in FIG. 5A to FIG. 7, an insert section 40 is composed of an elongated metallic pipe of short diameter. A first driving rod 41 and a second driving rod 42 that are made of metallic rods of short diameter are inserted into this pipe in parallel to each other. The first driving rod 41 is disposed eccentrically more upward than the axial center of the insert section 40. The second and third driving rods 42 and 43 are disposed symmetrically more downward than the axial center of the insert section 13, and is retractable independently in an axial direction.

A support section 44 having its rigidity that protrudes forward is integrally provided at the tip end of the insert section 40. A slitting 44a is provided at the tip end of the support section 44. To this slitting 44a, there is connected a turn plate 44a that turns in a traverse direction about a pivot 44b orthogonal to the axial direction of the insert section 40. To the turn plate 44c, a first pivot pin 45 is fixed in the direction orthogonal to the pivot 44b. To this first pivot pin 45, the proximal end of the first jaw 46 is turnably pivoted about this first pivot pin 45. A bent section 46a is provided at the proximal end of the first jaw 46 so that the second and third driving rods 42 and 43 are connected to this bent section 46a by means that will be described later.

A second jaw 49 is turnably connected at the intermediate part of the first jaw 46 by means of a second pivot pin 48, and the first jaw 46 and the second jaw 49 are turnable with the second pivot pin 48 being a fulcrum. The proximal end of the second jaw 49 is turnably connected to one end of the first connecting member 51 via the first connecting pin 50, and the other end of the first connecting member 51 is connected to the second connecting member 52 via a pivot pin 51a in the traverse direction. The other end of the second connecting member 52 is turnably connected at the tip end of the first driving rod 41 via a connecting pin 52a.

In addition, a third connecting member 56 is connected to a bent section 46a of the first jaw 46 via a third connecting pin 55. The proximal end of this third connecting member 56 is wide in the transverse direction. At this proximal end, the fourth connecting pin 57 and the fifth connecting pin 58 are provided to be spaced in the transverse direction. The fourth connecting pin 57 is connected to the second driving rod 42, and the fifth connecting pin 58 is connected to the third driving rod 43.

According to the thus configured slave manipulator, when the first driving rod 41 is advanced, the proximal end of the second jaw 49 is pushed forward via the first and second connecting members 51 and 52. Thus, the second jaw 49 turns with the second pivot pin 48 being a fulcrum, and the first and second jaws 46 and 419 open. Conversely, when the first driving rod 1 is retracted, the proximal end of the second jaw 49 is pulled backward via the first and second connecting members 51 and 52. Thus, the second jaw 49 turns with the second pivot pin 48 being a fulcrum, and the first and second jaws 46 and 49 close.

In addition, when the second and third driving rods 42 and 43 are retracted simultaneously, and the first driving rod is advanced, the proximal end of the first jaw 46 is pulled backward via the third connecting member 56. Thus, the first jaw 46 turns with the first pivot pin 45 being a fulcrum, and the second jaw 49 turns in the same direction with the first connecting pin 50 being a fulcrum, whereby the first and second jaws 46 and 49 can be turned at a substantial right angle relevant to the axle of the insert section 40.

In addition, from this state, when the first driving rod 41 is advanced, the proximal end of the second jaw 49 is pushed forward via the first and second connecting members 51 and 52. Thus, the second jaw 49 turns with the second pivot pin 48 being a fulcrum, and the first and second jaws 46 and 49 open.

Next, when the second driving rod 42 is retracted, and the third driving rod 43 is advanced, a turn plate 4c turns in the counterclockwise direction with the pivot 44b being a fulcrum. Thus, as shown in alternate dot and dashed line in FIG. 7, the first and second jaws 46 and 49 turn in the counterclockwise direction with the pivot 44b being a fulcrum. Conversely, when the second driving rod 42 is advanced, and the third driving rod 43 is retracted, the turn plate 44c turns in the clockwise direction with the pivot 44b being a fulcrum. Thus, the first and second jaws 46 and 49 turns in the clockwise direction with the pivot 44b being a fulcrum.

According to the present embodiment, the first and second jaws 46 and 49 that are openable can be turned in the vertical and transverse directions, and the first and second jaws 46 and 49 can approach a target site easily, whereby the degree of freedom for treatment can be improved.

Figure 8:
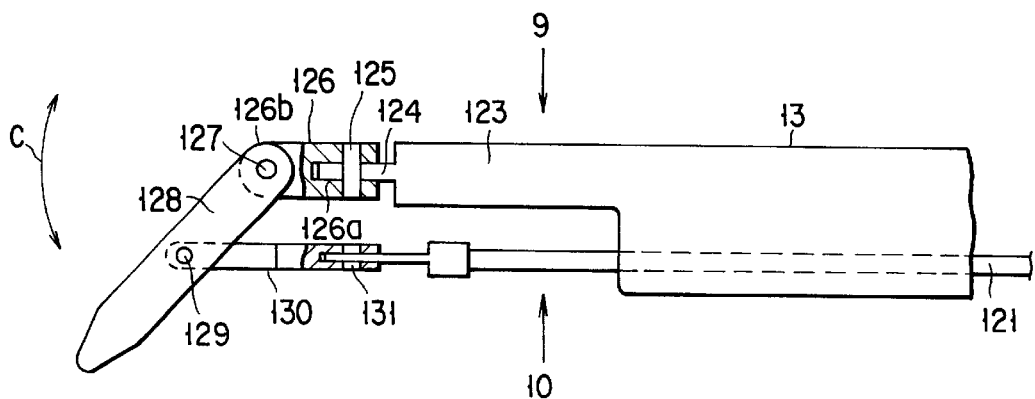
FIG. 8 is a side view having a partial cross section of essential portion of a slave manipulator according to a third embodiment of the present invention.
Figure 9:
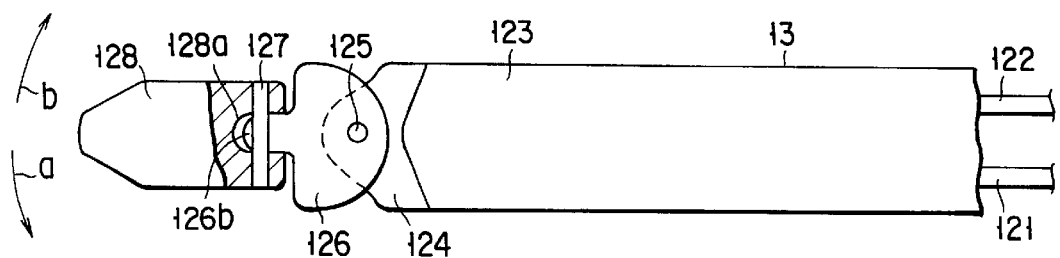
FIG. 9 is a view seen from the direction indicated by the arrow 9 shown in FIG. 8.
Figure 10:
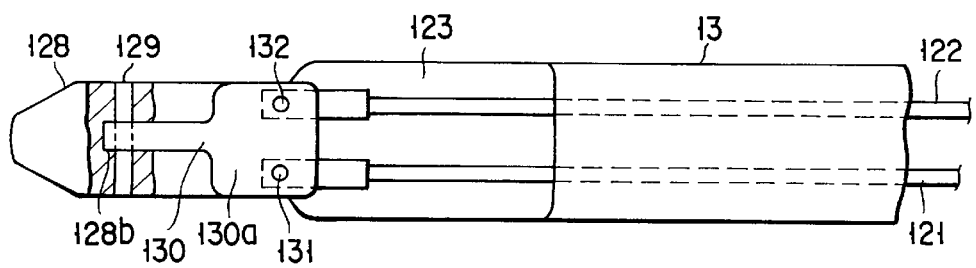
FIG. 10 is a view seen from the direction indicated by the arrow 9 shown in FIG. 8.

FIG. 8 to FIG. 10 show a third embodiment of the present invention. As illustrated, in a slave manipulator 12 of the present embodiment, the insert section 13 is composed of an elongated metallic pipe of short diameter. A first driving rod 121 and a second driving rod 122 that are made of metallic rods of short diameter are inserted into this pipe in parallel to each other. These first and second driving rods 121 and 122 are disposed symmetrically at both sides at an eccentric position more downward than the axial center part of the insert section 13, and is retractable independently in the axial direction.

At the tip end of the insert section 13, there is provided a protrusion 123 having its rigidity, the protrusion protruding forward at the upper side of the insert section 13 by cutting its lower side. A support section 124 is provided integrally at the tip end of this protrusion 123. A first pivot pin 125 that penetrate in the vertical direction is fixed to the support section 124. The proximal end of a first connecting member 126 is turnably pivoted at both ends of this first pivot pin 125. That is, a slitting 126a is provided at the proximal end of the first connecting member 126. The support section 124 is connected at this slitting 126a by means of the first connecting member 126 with the support section being sandwiched in the vertical direction.

The first connecting member 126 is short in a longitudinal direction. A protrusion 126b is provided integrally at the intermediate part in the transverse direction at its tip end, and the intermediate part of the second pivot pin 127 that penetrates in the transverse direction is provided at this protrusion 126b. In this manner, a second pivot pin 127 is provided at the tip end rather than the first pivot pin 125 and in the vicinity of the first pivot pin 125. At this second pivot pin 127, the proximal end of a tip end acting member 128 is turnably pivoted in the vertical direction. The tip end acting member 128 is a metallic rod-like member. A slitting 128a is provided at the proximal end of this member. At this slitting 128a, the protrusion 126b is connected while the protrusion 126b is sandwiched between the tip end acting members 128 in the transverse direction. Therefore, the tip end acting member 128 is turnable in the transverse direction with the first pivot pin 125 being a fulcrum, and is turnable in the vertical direction with the second pivot pin 127 being a fulcrum.

Further, one end of a second connecting member 130 is connected at the substantial intermediate part in the longitudinal direction of the tip end acting member 128 via a first connecting pin 129. That is, a slitting 128b is also provided at the intermediate part of the tip end acting member 128. The tip end of the second connecting member 130 is connected to this slitting 128b by means of a first connecting pin 129 while the tip end is inserted.

A wide section 130a that extends in the transverse direction is provided at the proximal end of the second connecting member 130. A second connecting pin 131 and a third connecting pin 132 are provided at both ends at the right and left of this wide section 130a. The first driving rod 121 is connected to the second connecting pin 131, and a second driving rod 122 is connected to a third connecting pin 132.

According to the thus configured slave manipulator 12, the first driving rod 121 is retracted, and the second driving rod 122 is advanced, whereby the tip end acting member 128 turns in the counterclockwise direction (in the direction indicated by the arrow 'a') with the pivot pin 125 being a fulcrum. The first driving rod 121 is advanced, and the second driving rod 122 is retracted, whereby the tip end acting member 128 turns in the clockwise direction (the direction indicated by the arrow 'b') with the first pivot pin 125 being a fulcrum. Further, the first and second driving rods 121 and 122 are advanced or retracted simultaneously, the tip end acting member 128 turns in the vertical direction (the direction indicated by the arrow 'c') with the second pivot pin 127 being a fulcrum.

Therefore, the tip end acting member 128 can approach a target site easily. In addition, the tip end acting member 128 is turned in the transverse direction or turned in the vertical direction, whereby a tissue can be released or pushed. In addition, a high frequency current is supplied to the tip end acting member 128, thereby making it possible to employ the member as a high frequency knife for coagulating or dissecting the tissue. Further, a pair of the tip end acting members 128 is made openable, whereby treatment can be performed such that a tissue is gripped or a suture needle is griped, thereby suturing a dissected site.

Although the advancement or retraction of the first and second driving rods 121 and 122 is driven by converting a rotational movement of the servo motor 16 incorporated in the slave driving section 15 into a linear movement by means of a wire provided inside of the slave driving section 15 and a pulley having the wire hung thereon (not shown), means for advancing and retracting the first and second driving rods 121 and 122 is not limited.

As has been described above, according to the present invention, the first and second driving rods are operated to be advanced or retracted, whereby the first and second jaws (tip end acting members) can be directionally changed in the axial direction of the insert section and relevant to the axle. Moreover, in any state as well, the first and second jaws can be opened or closed. Therefore, approach properties for a target site are improved, and the degree of freedom for treatment can be improved.

Further, the first and second jaws (tip end acting members) are driven by operating the first and second driving rods to be advanced or retracted, whereby a force twice as much as usual can be obtained, and an operational failure due to wire expansion or the like does not occur. There is an advantageous effect that, even if external force is applied to the first and second jaws (tip end acting members), these jaws do not move, and reliable treatment can be performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical operation apparatus comprising:
   an insert section to be inserted into a body;
   a first jaw that has a first grip section, and that turns about a first pivot provided at a tip end of said insert section;
   a second jaw that has a second grip section, and that turns about a second pivot provided at said first jaw, said second grip section forming a contacted/spaced face to be contacted or spaced relevant to a grip object in collaboration with said first grip section;
   a first driving rod connected to said first jaw, said first driving rod being advanced and retracted along said insert section, thereby turning said first jaw;
   a second driving rod connected to said second jaw, said second driving rod being advanced or retracted along said insert section, thereby turning said second jaw; and
   driving means provided at a proximal end of said insert section, said driving means being adapted to drive said first and second driving rods to be advanced or retracted.

2. A surgical operation apparatus comprising:
   an insert section to be inserted into a body;
   a first jaw that has a first grip section, and that turns about a first pivot provided at a tip end of said insert section;

a second jaw that has a second grip section, and that turns about a second pivot provided at said first jaw, said second grip section forming a contacted/spaced face to be contacted or spaced relevant to a grip object in collaboration with said first grip section;

a first driving rod connected to a first connecting section provided at a site of said first jaw positioned between said first pivot and said second pivot, said first driving rod being advanced or retracted along said insert section, thereby turning said first jaw about said first pivot;

a connecting member connected to a second connection section provided at a proximal end of said second jaw;

a second driving rod connected to a third connecting section provided at the proximal end of said second jaw, said second driving rod being advanced or retracted along said insert section, thereby turning said second jaw about said second pivot; and driving means provided at the proximal end of said insert section, said driving means being adapted to drive said first and second driving rods to be advanced or retracted.

3. A surgical operation apparatus according to claim 2, wherein said second pivot is provided at a tip end rather than said first pivot.

4. A surgical operation apparatus according to claim 2, wherein said first connecting section is provided at the tip end rather than said first pivot.

5. A surgical operation apparatus according to claim 2, wherein said third connecting section is positioned in opposite to said first connecting section relevant to said first pivot.

6. A surgical operation apparatus according to claim 2, wherein said first jaw is turnable in the range of substantially 90 degrees about said first pivot by advancement or retraction of said first driving rod, and can be maintained at an arbitrary position within said turning range.

7. A surgical operation apparatus according to claim 6, wherein, when said second jaw is turned by advancement or retraction of said second driving rod while a position of said first jaw is maintained, said first and second grip sections open or close.

8. A surgical operation apparatus according to claim 2, wherein said surgical operation apparatus is a slave manipulator driven in accordance with an operation of a master manipulator.

9. A surgical operation apparatus according to claim 2, wherein said contacted/spaced face is formed so as to suture a tissue of a living body by gripping a suture needle.

10. A surgical operation apparatus comprising:

an insert section to be inserted into a body;

a first connecting member that turns about a first pivot provided at a tip end of said insert section;

a second pivot provided at said first connecting member in a direction orthogonal to said first pivot;

a first jaw that has a first grip section, and that turns about said second pivot;

a second jaw that has a second grip section, and that turns about a third pivot provided at said first jaw, said second grip section forming a contacted/spaced face to be contacted or spaced relevant to a grip object in collaboration with said first grip section;

a first connecting section provided at said first jaw;

a second connecting member connected to said first connecting section, from which said second connecting member extends toward a proximal end of said apparatus;

second and third connecting sections provided at a proximal end of said second connecting member, the second and third connection sections being positioned each other side by side in a direction orthogonal to an extension direction of said second connecting member;

first and second driving rods connected to said second and third connecting sections, the first and second driving rods being able to advance and retract along said insert section, wherein, when one of said first and second driving rods is advanced toward the tip end, and the other is retracted toward the proximal end of said apparatus, said first jaw turns about said first pivot, and when said first and second driving rods are advanced or retracted simultaneously, said tip end member turns about said second pivot;

a fourth connecting section provided at a proximal end of said second jaw;

a third connecting member connected to said fourth connecting section;

a fifth connecting section provided at a proximal end of said third connecting member;

a third driving rod connected to said fifth connecting section, said third driving rod being able to advance or retract along said insert section, said third driving rod turning said second jaw about said third pivot;

driving means provided at a proximal end of said insert section, the driving means being adopted to drive said first, second, and third driving rods to be advanced or retracted.

11. A surgical operation apparatus according to claim 10, wherein said second pivot is provided at the tip end rather than said first pivot.

12. A surgical operation apparatus according to claim 10, wherein said first connecting section is provided at the tip end rather than said first pivot.

13. A surgical operation apparatus according to claim 10, wherein said fourth connecting section is provided in opposite to said first connecting section relevant to said first pivot.

14. A surgical operation apparatus according to claim 10, wherein said second pivot is provided at the tip end rather than said first pivot and in the vicinity of said first pivot.

15. A surgical operation apparatus according to claim 10, wherein said first connecting section is provided at the tip end rather than said first pivot.

16. A surgical operation apparatus according to claim 10, wherein said first and second driving rods are provided symmetrically at both sides of an axial center of the insert section.

17. A surgical operation apparatus according to claim 10, wherein said surgical operation apparatus is a slave manipulator to be driven in accordance with an operation of a master manipulator.

18. A surgical operation apparatus according to claim 10, wherein said contacted/spaced face is formed so as to suture a tissue of a living body by gripping a suture needle.

\* \* \* \* \*